(12) United States Patent
Abravaya et al.

(10) Patent No.: US 10,457,981 B2
(45) Date of Patent: Oct. 29, 2019

(54) HYBRIDIZATION BUFFERS

(71) Applicant: Abbott Molecular Inc., Des Plaines, IL (US)

(72) Inventors: Klara Abravaya, Des Plaines, IL (US); Madhuri Lucas, Des Plaines, IL (US); Ekaterina Pestova, Des Plaines, IL (US); Adam Koch, Des Plaines, IL (US); Kimberly Wilber-Mader, Des Plaines, IL (US)

(73) Assignee: Abbott Molecular Inc., Des Plaines, IL (US)

(*) Notice: Subject to any disclaimer, the term of this patent is extended or adjusted under 35 U.S.C. 154(b) by 125 days.

(21) Appl. No.: 15/256,146

(22) Filed: Sep. 2, 2016

(65) Prior Publication Data

US 2017/0198341 A1 Jul. 13, 2017

Related U.S. Application Data

(60) Provisional application No. 62/276,465, filed on Jan. 8, 2016.

(51) Int. Cl.
 *C12Q 1/68* (2018.01)
 *C12Q 1/6841* (2018.01)

(52) U.S. Cl.
 CPC ................ *C12Q 1/6841* (2013.01)

(58) Field of Classification Search
 USPC .......... 435/6.1, 6.11, 91.1; 436/94, 501; 536/23.1, 24.3, 24.33
 See application file for complete search history.

(56) References Cited

U.S. PATENT DOCUMENTS

| | | | | |
|---|---|---|---|---|
| 4,689,294 A * | 8/1987 | Boguslawski | ....... | C12Q 1/6832 435/6.12 |
| 5,759,777 A | 6/1998 | Kearney et al. | | |
| 8,624,020 B2 | 1/2014 | Himmelreich et al. | | |
| 2003/0165918 A1* | 9/2003 | Nakamura | ........... | C12Q 1/6818 435/6.11 |
| 2004/0254101 A1 | 12/2004 | Dillon et al. | | |
| 2005/0256076 A1* | 11/2005 | Bumcrot | .............. | C12N 15/113 514/44 A |
| 2006/0057576 A1* | 3/2006 | Paszkowski | .......... | B01L 3/5027 435/6.11 |
| 2007/0099188 A1* | 5/2007 | Boeke | ................... | C12Q 1/6827 435/6.16 |
| 2007/0161019 A1* | 7/2007 | Inazawa | ............... | C12Q 1/6886 435/6.12 |
| 2011/0281263 A1* | 11/2011 | Matthiesen | .......... | C12Q 1/6832 435/6.11 |
| 2013/0203055 A1 | 8/2013 | Aurich-Costa | | |
| 2014/0234844 A1 | 8/2014 | Matthiesen | | |
| 2015/0064701 A1 | 3/2015 | Aurich-Costa et al. | | |
| 2017/0067094 A1 | 3/2017 | Wilber-Mader | | |

FOREIGN PATENT DOCUMENTS

| | | |
|---|---|---|
| EP | 0184017 | 6/1986 |
| WO | 89/02934 | 4/1989 |
| WO | 96/00234 | 1/1996 |
| WO | 98/13527 | 4/1998 |
| WO | 99/60163 | 11/1999 |
| WO | 02/083672 | 10/2002 |
| WO | 2004/058300 | 7/2004 |
| WO | 2006/083925 | 8/2006 |
| WO | 2009/051776 | 4/2009 |
| WO | 2011/134474 | 11/2011 |
| WO | 2013/046033 | 4/2013 |
| WO | 2013/144986 | 10/2013 |
| WO | 2015/007800 | 1/2015 |

OTHER PUBLICATIONS

Powell R D et al., "Metallographic in situ hybridization," Hum. Pathol., 38:1145-59 (2007).
Chen et al., "A Plasmodium falciparum-specific reverse target capture assay," Molecular and Biochemical Parasitology, 1991, vol. 44, No. 2, pp. 165-173.
Dave et al., "Fast Molecular Beacon Hybridization in Organic Solvents with Improved Target Specificity," Journal of Physical Chemistry Part A Condensed Matter, Materials, Surfaces, Interfaces & Biophysical, 2010, vol. 114, No. 47, pp. 15694-15699.
International Search Report and Written Opinion for Application No. PCT/US2016/050220 dated Nov. 21, 2016 (16 pages).
International Search Report and Written Opinion for Application No. PCT/US2016/050232 dated Nov. 22, 2016 (17 pages).
Mattiesen et al., "Fast and Non-Toxic in Situ Hybridization without Blocking of Repetitive Sequences," PLOS ONE, 2012, vol. 7, No. 7, pp. e40675-1.
Morrissey et al., "Nucleic acid hybridization assays employing dA-tailes capture probes—I. Multiple capture methods," Analytical Biochemistry, 1989, vol. 181, No. 2, pp. 345-359.
Tao et al., "Room-Temperature Hybridization of Target DNA with Microarrays in Concentrated Solutions of Guanidine Thiocyanate," Biotechniques, 2003, vol. 34, No. 6, pp. 1260-1262.
Wilber et al., "Assessment of a new FISH hybridization buffer that enables fast-track: Single shift FISH results," Virchows Archly, 2015, vol. 467, No. Suppl. 1, p. S164.
United States Patent Office Action for U.S. Appl. No. 15/256,081 dated Sep. 1, 2017 (8 pages).

* cited by examiner

*Primary Examiner* — Frank W Lu

(74) *Attorney, Agent, or Firm* — Casimir Jones, S.C.; Melissa Kolom

(57) ABSTRACT

Disclosed herein are hybridization buffer compositions and hybridization compositions, methods of making the compositions, and methods of using the compositions, such as the hybridization of DNA or RNA sequences by fluorescence in situ hybridization ("FISH").

17 Claims, No Drawings

HYBRIDIZATION BUFFERS

CROSS-REFERENCE TO RELATED APPLICATIONS

This patent application claims the benefit of U.S. Provisional Patent Application No. 62/276,465, filed Jan. 8, 2016, which is incorporated by reference herein.

TECHNICAL FIELD

The present disclosure relates generally to hybridization buffers for labeling of genomic DNA and RNA. More particularly, the present disclosure relates to hybridization buffer compositions useful in conjunction with biologic and synthetic probes for hybridizing DNA or RNA sequences by fluorescence in situ hybridization ("FISH") and blot hybridization methodologies.

BACKGROUND

Hybridization is a phenomenon in which single-stranded deoxyribonucleic acid (DNA) or ribonucleic acid (RNA) molecules anneal to complementary DNA or RNA. Though a double-stranded DNA sequence is generally stable under physiological conditions, changing these conditions in the laboratory (generally by raising the surrounding temperature) will cause the molecules to separate into single strands. These strands are complementary to each other but may also be complementary to other sequences present in their surroundings. Lowering the surrounding temperature allows the single-stranded molecules to anneal or "hybridize" to each other.

Hybridization is useful in numerous molecular biology techniques including Southern blots and Northern blots, and most approaches to DNA sequencing. Overall, genetic relatedness of two species can be determined by hybridizing segments of their DNA (DNA-DNA hybridization). Due to sequence similarity between closely related organisms, higher temperatures are required to melt such DNA hybrids when compared to more distantly related organisms. A variety of different methods use hybridization to pinpoint the origin of a DNA sample, including polymerase chain reaction (PCR). In another technique, short DNA sequences are hybridized to cellular mRNAs to identify expressed genes. Researchers are also exploring the use of antisense RNA to bind to undesired mRNA, preventing the ribosome from translating the mRNA into protein.

Fluorescence in situ hybridization (FISH) is a technique that uses fluorescent probes that bind to only those parts of the chromosome with a high degree of sequence complementarity. It is used to detect and localize the presence or absence of specific DNA sequences on chromosomes. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues.

In order to efficiently and effectively perform techniques such as FISH, robust experimental conditions are desired to provide reproducible and reliable results. Accordingly, there exists a need for reliable reaction media and conditions to perform these experiments.

SUMMARY

In one aspect, disclosed is a hybridization buffer composition comprising an accelerating agent, a buffering agent, a solvent and guanidinium thiocyanate.

In another aspect, disclosed is a hybridization composition comprising a hybridization buffer composition comprising an accelerating agent, a buffering agent, a solvent and guanidinium thiocyanate; and at least one nucleic acid sequence.

Also disclosed are methods of making and using the hybridization buffer and hybridization compositions.

DETAILED DESCRIPTION

The present disclosure relates to hybridization buffer compositions, methods for preparing the compositions and methods of using the compositions. The disclosed hybridization buffer compositions include at least one accelerating agent, at least one buffering agent, at least one solvent, and guanidinium thiocyanate. The hybridization buffer composition may also include a polyacrylate. The hybridization buffer composition may be combined with one or more nucleic acid sequences to form a hybridization composition.

The combination of the components of the hybridization buffer composition results in a buffer composition that is useful as a hybridization reagent. The buffer composition may be useful in assays that require the labeling of genomic DNA and RNA. The buffer may be useful in conjunction with biologic and synthetic probes for hybridizing DNA or RNA sequences by fluorescence in situ hybridization ("FISH") and blot hybridization methodologies. The combination of specific components of the buffer composition (e.g. accelerating agent, buffering agent, solvent and guanidinium thiocyanate) provides a composition that is an unexpectedly superior buffer composition.

For example, the use of higher concentrations of accelerating agents such as dextran sulfate may facilitate FISH assays to be complete in shorter time periods compared to existing buffer compositions. The use of guanidinium thiocyanate may also be useful in lowering the occurrence of probe hybridization to unintended targets, thereby improving the specificity and background signal of the assay readouts.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," consisting of" and "consisting essentially of," the embodiments or elements presented herein, whether explicitly set forth or not.

"Nucleic acid," "nucleic acid chain," and "nucleic acid sequence" mean anything that binds or hybridizes using base pairing including, oligomers or polymers having a backbone formed from naturally occurring nucleotides and/or nucleic acid analogs comprising nonstandard nucleobases and/or nonstandard backbones (e.g., a peptide nucleic acid (PNA) or locked nucleic acid (LNA)), or any derivatized form of a nucleic acid.

As used herein, the term "peptide nucleic acid" or "PNA" means a synthetic polymer having a polyamide backbone with pendant nucleobases (naturally occurring and modified). The pendant nucleobase, such as a purine or pyrimidine base on PNA may be connected to the backbone via a linker. In one embodiment, the PNA has an N-(2-aminoethyl)-glycine) backbone. PNAs may be synthesized and optionally labeled. PNAs hybridize tightly, and with high sequence specificity, with DNA and RNA, because the PNA backbone is uncharged. Thus, short PNA probes may exhibit comparable specificity to longer DNA or RNA probes. PNA probes may also show greater specificity in binding to complementary DNA or RNA.

As used herein the term "locked nucleic acid" or "LNA" means an oligomer or polymer comprising at least one or more LNA subunits. As used herein, the term "LNA subunit" means a ribonucleotide containing a methylene bridge that connects the 2'-oxygen of the ribose with the 4'-carbon.

Examples of nucleic acids and nucleic acid analogs also include polymers of nucleotide monomers, including double and single stranded deoxyribonucleotides (DNA), ribonucleotides (RNA), α-anomeric forms thereof, synthetic and natural analogs thereof, and the like. The nucleic acid chain may be composed entirely of deoxyribonucleotides, ribonucleotides, peptide nucleic acids (PNA), locked nucleic acids (LNA), synthetic or natural analogs thereof, or mixtures thereof DNA, RNA, or other nucleic acids as defined herein can be used in the method and compositions of the disclosure.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. The Compositions

A. Hybridization Buffer Composition

The disclosed hybridization buffer compositions include at least one accelerating agent, at least one buffering agent, at least one solvent, and guanidinium thiocyanate. The hybridization buffer compositions may further include polyacrylate. This combination of components provides buffer compositions that can be used as hybridization reagents. The buffer compositions may be useful in assays that require the labeling of genomic DNA and RNA. The buffer compositions may be useful in conjunction with biologic and synthetic probes for hybridizing DNA or RNA sequences by fluorescence in situ hybridization ("FISH") and blot hybridization methodologies. The buffer compositions may promote hybridization of fluorescently labeled molecular probes to occur faster than existing methods.

For example, the use of higher concentrations of accelerating agents such as dextran sulfate may facilitate FISH assays to be complete in shorter time periods compared to existing buffer compositions. The use of guanidinium thiocyanate may also be useful in lowering the occurrence of probe hybridization to unintended targets, thereby improving the specificity and background signal of the assay readouts.

The hybridization buffer compositions may have a pH of about 3.0 to about 9.0, about 3.0 to about 8.5, about 3.5 to about 8.5, about 3.5 to about 8.0, about 4.0 to about 8.0, about 4.5 to about 8.0, about 5.0 to about 8.0, about 5.5 to about 8.0, about 6.0 to about 8.0, about 6.0 to about 7.5, about 6.5 to about 7.5 or about 7.0 to about 7.5. The hybridization buffer compositions may have a pH of about 3.0, about 3.5, about 4.0, about 4.5, about 5.0, about 5.5, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.5 or about 9.0.

1. Accelerating Agent

The buffer compositions include at least one accelerating agent. The accelerating agent is capable of accelerating hybridization rates of nucleic acids.

The accelerating agent may be a polymer such as ficoll, polyvinylpyrrolidone (PVP), heparin, or dextran sulfate. The accelerating agent may be a protein such as bovine serum albumin (BSA). The accelerating agent may be a glycol such as ethylene glycol, glycerol, 1,3 propanediol, propylene glycol, or diethylene glycol. The accelerating agent may be an organic solvent such as formamide, dimethylformamide, or dimethylsulfoxide. The accelerating agent may be a combination of any of the accelerating agents listed herein such as Denhardt's solution.

In certain embodiments, the accelerating agent is dextran sulfate. Dextran sulfate is an anionic polymer of sulfated glucose, capable of accelerating hybridization rates of nucleic acids. The polyanionic character of dextran sulfate helps to approximate nudeis acid strands, increasing their effective concentration to each other and promoting hybridization. Dextran sulfate also demonstrates a sequestering interaction with proteins, presumably through hydrogen-bonding between the sulfate groups and amine groups of the protein that generates an insoluble complex. The ability of the polymer to precipitate fibrinogen and low-density lipoproteins from plasma solutions has been used for analysis and for anticoagulant applications. Use of higher dextran sulfate concentrations, in comparison to existing buffer compositions, may facilitate FISH assays to be complete in shorter time periods.

The hybridization buffer compositions may comprise about 10% (w/v) to about 40% (w/v), about 10% (w/v) to about 30% (w/v), about 20% (w/v) to about 30% (w/v), about 24% (w/v) to about 32% (w/v), about 24% (w/v) to about 29%(w/v), or about 28% (w/v) to about 30% (w/v) of the accelerating agent. The hybridization buffer compositions may comprise, by weight, about 10% (w/v), about 15% (w/v), about 20% (w/v), about 21% (w/v), about 22% (w/v), about 23% (w/v), about 24% (w/v), about 25% (w/v), about 26% (w/v), about 27% (w/v), about 28% (w/v), about 29% (w/v), about 30% (w/v), about 31% (w/v), about 32% (w/v), about 33% (w/v), about 34% (w/v), about 35% (w/v) or about 40% (w/v) of the accelerating agent.

2. Buffering Agent

The hybridization buffer compositions include at least one buffering agent. A buffering agent is a weak acid or base used to maintain the acidity (pH) of a solution near a chosen value after the addition of another acid or base. That is, the function of a buffering agent is to prevent a rapid change in pH when acids or bases are added to the solution. The buffering agent of the disclosed hybridization buffer is capable of maintaining the pH of the buffer composition at or near physiological pH.

The buffering agent may be saline sodium citrate (SSC), 4-(2-hydroxyethyl)-1-piperazineethanesulfonic acid (HEPES), SSPE, piperazine-N,N'-bis(2-ethanesulfonic acid) (PIPES), tetramethyl ammonium chloride (TMAC), Tris (hydroxymethyl)aminomethane (Tris), SET (sucrose/EDTA/Tris), citric acid, potassium phosphate or sodium pyrophosphate.

In certain embodiments, the buffering agent is saline sodium citrate (SSC), a standard reagent in certain hybridization procedures. SSC may be used to control stringency of wash buffer for the washing steps after hybridization. This buffering agent combines sodium citrate and sodium chloride, which allows it to maintain the pH of the hybridization buffer composition at a specific pH, which includes at or near physiological pH.

In certain embodiments, SSC comprises a mixture of 3 M NaCl and 0.3 M sodium citrate at a pH of 7.0, known as 20×SSC. 20×SSC may be diluted to provide the mixture of NaCl and sodium citrate in lower concentrations. For example, 2×SSC is a solution of 20× SSC diluted by a factor of 10, resulting in a solution with 0.3 M (300 mM) NaCl and 0.03 M (30 mM) sodium citrate. Likewise, 0.5×SSC is a solution of 20×SSC diluted by a factor of 40, resulting in a solution with 0.075 M (75 mM) NaCl and 0.0075 M (7.5 mM) sodium citrate.

The hybridization buffer compositions may comprise about 5 mM to about 100 mM, about 5 mM to about 20 mM, about 5 mM to about 15 mM, or about 5 mM to about 10 mM of the buffering agent. The hybridization buffer compositions may comprise about 5 mM, about 6 mM, about 7 mM, about 7.5 mM, about 8 mM, about 9 mM, about 10 mM, about 15 mM, about 20 mM, about 25 mM, about 30 mM, about 35 mM, about 40 mM, about 45 mM, about 50 mM, about 60 mM, about 70 mM, about 75 mM, about 80 mM, about 90 mM, or about 100 mM of the buffering agent.

In certain embodiments, the concentration recited for the buffering agent refers to the concentration of sodium citrate in the buffer. When using SSC, NaCl is also present at a concentration that is a factor of 10 greater than the concentration of sodium citrate.

The hybridization buffer composition may comprise about 5 mM to about 100 mM, about 5 mM to about 50 mM, about 5 mM to about 20 mM, about 5 mM to about 15 mM, or about 5 mM to about 10 mM sodium citrate. The hybridization buffer composition may comprise about 5 mM, about 6 mM, about 7 mM, about 7.5 mM, about 8 mM, about 9 mM, about 10 mM, about 15 mM, about 20 mM, about 25 mM, about 30 mM, about 35 mM, about 40 mM, about 45 mM, about 50 mM, about 60 mM, about 70 mM, about 80 mM, about 90 mM, or about 100 mM sodium citrate.

The hybridization buffer composition may comprise about 50 mM to about 500 mM, about 50 mM to about 100 mM, about 50 mM to about 90 mM, about 50 mM to about 80 mM, about 60 mM to about 80 mM, about 60 mM to about 75 mM, or about 70 mM to about 80 mM sodium chloride. The hybridization buffer composition may comprise about 50 mM, about 55 mM, about 60 mM, about 65 mM, about 70 mM, about 75 mM about 80 mM, about 85 mM, about 90 mM, about 100 mM, about 200 mM, about 300 mM, about 400 mM, or about 500 mM sodium chloride.

3. Solvent

The buffer composition includes at least one solvent. The solvent is chosen such that it preferably solubilizes all other components of the composition, thus forming a homogeneous solution. In certain embodiments, the solvent is a polar aprotic solvent. In general, a polar aprotic solvent is a solvent that does not have a hydrogen that is readily exchanged at physiological pH and has a dielectric constant of at least 5 at a temperature of 18-25° C., as defined in the CRC Handbook of Chemistry and Physics, 95$^{th}$ edition.

The solvent may be formamide, dimethylformamide, dimethylsulfoxide or acetonitrile, or a combination thereof.

In certain embodiments, the solvent is formamide. Formamide may be useful in the hybridization buffer composition because it may lower the melting point and annealing temperature of nucleic acid -strands in in situ hybridization. A useful property of formamide is better preservation of morphology due to a lower incubation temperature.

The hybridization buffer composition may comprise, by volume, about 10% to about 50%, about 20% to about 50%, about 30% to about 40%, about 35% to about 45%, or about 38% to about 42% of the solvent. The hybridization buffer composition may comprise, by volume, about 10%, about 15%, about 20%, about 25%, about 30%, about 33%, about 35%, about 40%, about 45%, or about 50% of the solvent.

4. Guanidinium Thiocyanate

The buffer composition includes guanidinium thiocyanate. Inclusion of guanidinium thiocyanate aides in lowering the occurrence of probe hybridization to unintended targets (non-specific or background signal).

The hybridization buffer composition may comprise about 0.3 M to about 2.0 M, about 0.4 M to about 2.0 M, about 0.4 M to about 1.6 M, or about 1.0 M to about 1.6 M guanidinium thiocyanate. The hybridization buffer composition may comprise about 0.3 M, about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, or about 2.0 M guanidinium thiocyanate.

5. Polyacrylate

The buffer composition may include a polyacrylate. The polyacrylate may function as a volume excluder.

The polyacrylate may be sodium polyacrylate, a sodium salt of polyacrylic acid with the chemical formula $[-CH_2-CH(CO_2Na)-]_n$. The number of repeating units, n, may be such that the average molecular weight of the sodium polyacrylate is between about 1,500 g/mol and about 10,000 g/mol. The average molecular weight of the sodium polyacrylate may be about 1,500 g/mol to about 6,000 g/mol, about 2,000 g/mol to about 6,000 g/mol, about 2,100 g/mol to about 5,100 g/mol, about 1,500 g/mol to about 2,500 g/mol, or about 4,500 g/mol to about 5,500 g/mol. The average molecular weight of the sodium polyacrylate may be about 1,500 g/mol, about 2,000 g/mol, about 2,100 g/mol, about 2,500 g/mol, about 3,000 g/mol, about 3,500 g/mol, about 4,000 g/mol, about 4,500 g/mol, about 5,000 g/mol, about 5,100 g/mol, about 5,500 g/mol, about 6,000 g/mol, about 7,000 g/mol, about 8,000 g/mol, about 9,000 g/mol or about 10,000 g/mol.

The hybridization buffer composition may comprise about 5% (w/v) to about 20% (w/v), about 5% (w/v) to about 15% (w/v), or about 8% (w/v) to about 12% (w/v) of the polyacrylate. The hybridization buffer composition may comprise, by weight, about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), or about 20% (w/v) of the poly acry late.

In certain embodiments, the hybridization buffer composition comprises about 28.8% (w/v) dextran sulfate, about 6 mM sodium citrate, about 60 mM sodium chloride, about 40% (v/v) formamide, and about 1.6 M guanidinium thiocyanate.

In certain embodiments, the hybridization buffer composition comprises about 32% (w/v) dextran sulfate, about 6 mM sodium citrate, about 60 mM sodium chloride, about 40% (v/v) formamide, and about 1.6 M guanidinium thiocyanate.

In certain embodiments, the hybridization buffer composition comprises about 24% (w/v) dextran sulfate, about 7.5 mM sodium citrate, about 75 mM sodium chloride, about 33% (v/v) formamide, and about 1.0 M guanidinium thiocyanate.

In certain embodiments, the hybridization buffer composition comprises about 28% (w/v) dextran sulfate, about 7.5 mM sodium citrate, about 75 mM sodium chloride, about 30% (v/v) formamide, and about 1.0 M guanidinium thiocyanate.

In certain embodiments, the hybridization buffer composition comprises about 18% (w/v) dextran sulfate, about 15 mM sodium citrate, about 150 mM sodium chloride, about 33% (v/v) formamide, about 1.0 M guanidinium thiocyanate, and about 10% (w/v) sodium poly acrylate.

B. Hybridization Composition

The disclosed hybridization compositions include the hybridization buffer composition and at least one nucleic acid sequence. The hybridization composition may be useful in assays that require the labeling of genomic DNA and RNA. The hybridization composition may comprise biologic and/or synthetic probes for hybridizing DNA or RNA sequences by fluorescence in situ hybridization ("FISH") and blot hybridization methodologies.

In certain embodiments, the hybridization composition comprises a hybridization buffer composition comprising an accelerating agent, a buffering agent, a solvent, guanidinium thiocyanate, optionally a polyacrylate, and at least one nucleic acid sequence.

In certain embodiments, the hybridization composition comprises a hybridization buffer composition comprising an accelerating agent, a buffering agent, a solvent, guanidinium thiocyanate, and optionally a polyacrylate; a first nucleic acid sequence; and a second nucleic acid sequence. In certain embodiments, the first nucleic acid sequence is a molecular probe.

In certain embodiments, the hybridization composition comprises a hybridization buffer composition comprising about 10% (w/v) to about 30% (w/v) an accelerating agent, about 5 mM to about 40 mM a buffering agent, about 20% (v/v) to about 40% (v/v) a solvent, about 0.4 M to about 1.6 M guanidinium thiocyanate, and optionally about 5% (w/v) to about 20% (w/v) a polyacrylate; and at least one nucleic acid sequence.

In certain embodiments, the hybridization composition comprises a hybridization buffer composition comprising about 10% (w/v) to about 30% (w/v) an accelerating agent, about 5 mM to about 40 mM a buffering agent, about 20% (v/v) to about 40% (v/v) a solvent, about 0.4 M to about 1.6 M guanidinium thiocyanate, and optionally about 5% (w/v) to about 20% (w/v) a polyacrylate; a first nucleic acid sequence; and a second nucleic acid sequence. In certain embodiments, the first nucleic acid sequence is a molecular probe.

In certain embodiments, the hybridization composition comprises a hybridization buffer composition comprising about 10% (w/v) to about 30% (w/v) an accelerating agent, about 5 mM to about 40 mM a buffering agent, about 20% (v/v) to about 40% (v/v) a solvent, about 0.4 M to about 1.6 M guanidinium thiocyanate, and optionally about 5% (w/v) to about 20% (w/v) a polyacrylate; and at least 3 nucleic acid sequences. In certain embodiments, at least 2 of the nucleic acid sequences are molecular probes.

In certain embodiments, the hybridization composition comprises from 1 µL to 200 µL, 1 µL to 100 µL, 1 µL to 50 µL, 1 µL to 40 µL, 1 µL to 30µL, 1 µL to 20µL, 1 µL to 15 µL, 1 µL to 12 µL, or 1 µL to 10 µL of the hybridization buffer composition, and from 0.1 µL to 50 µL, 0.1 µL to 25 µL, 0.1 µL to 20 µL, 0.1 µL to 15 4, 0.1 4 to 10 µL, 0.1 µL to 5 µL, 0.1 µL to 4 µL, or 0.1 µL to 3 µL of a solution with at least one nucleic acid sequence.

In certain embodiments, the hybridization composition comprises 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 26 µL, 27 µL, 28 µL, 29 µL, 30 µL, 31 µL, 32 µL, 33 µL, 34 µL, 35 µL, 36 µL, 37 µL, 38 µL, 39 µL, 40 µL, 41 µL, 42 µL, 43 µL, 44 µL, 45 µL, 46 µL, 47 µL, 48 µL, 49 µL, 50 µL, 51 µL, 52 µL, 53 µL, 54 µL, 55 µL, 56 µL, 57 µL, 58 µL, 59 µL, 60 µL, 61 µL, 62 µL, 63 µL, 64 µL, 65 µL, 66 µL, 67 µL, 68 µL, 69 µL, 70 µL, 71 µL, 72 µL, 73 µL, 74 µL, 75 µL, 76 µL, 77 µL, 78 µL, 79 µL, 80 µL, 81 µL, 82 µL, 83 µL, 84 µL, 85 µL, 86 µL, 87 µL, 88 µL, 89 µL, 90 µL, 91 µL, 92 µL, 93 µL, 94 µL, 95 µL, 96 µL, 97 µL, 98 µL, 99 µL, 100 µL, 110 µL, 120 µL, 130 µL, 140 µL, 150 µL, 160 µL, 170 µL, 180 µL, 190 µL or 200 µL of the hybridization buffer composition, and 0.1 µL, 0.2 µL, 0.3 µL, 0.4 µL, 0.5 µL, 0.6 µL, 0.7 µL, 0.8 µL, 0.9 µL, 1 µL, 2 µL, 3 µL, 4 µL, 5 µL, 6 µL, 7 µL, 8 µL, 9 µL, 10 µL, 11 µL, 12 µL, 13 µL, 14 µL, 15 µL, 16 µL, 17 µL, 18 µL, 19 µL, 20 µL, 21 µL, 22 µL, 23 µL, 24 µL, 25 µL, 30 µL, 35 µL, 40 µL, 45 µL, or 50 µL of a solution with at least one nucleic acid sequence.

C. Methods of Using the Compositions

The methods and compositions of the disclosure may be used fully or partly in all types of hybridization applications in the fields of cytology, histology, or molecular biology.

In certain embodiments, the first or the second nucleic acid sequence in the methods of the disclosure is present in a biological sample. Examples of such samples include tissue samples, cell preparations, cell fragment preparations, nuclei and isolated or enriched cell component preparations. The sample may originate from various tissues such as breast, lung, colorectal, prostate, lung, head & neck, stomach, pancreas, esophagus, liver, and bladder, or other relevant tissues and neoplasia thereof, any cell suspension, blood sample, bone marrow, peripheral blood mononuclear cells, bone marrow mononuclear cells, plasma cell enriched specimens, fine needle aspiration, ascites fluid, sputum, peritoneum wash, lung wash, urine, feces, cell scrape, cell smear, cytospin or cytoprep cells.

The sample may be isolated and processed using standard protocols. Tissue and cell samples may be obtained using conventional methods such as surgical resection, biopsy, fine needle aspiration, brushing, washes, barbotage, smears, touch preparations of the tissue, bone marrow aspiration, blood sampling, amniotic sampling, and similar methods. The isolated sample may be treated in many different ways depending on the purpose of obtaining the sample and depending on the routine at the site. Often the sample is treated with various reagents to preserve the tissue for later sample analysis, alternatively the sample may be analyzed directly. Examples of widely used methods for preserving samples are methanol:acetic acid fixation or formalin-fixed followed by paraffin-embedding and cryo-preservation.

For metaphase spreads, cell cultures are generally treated with colcemid, or another suitable spindle pole disrupting agent, to stop the cell cycle in metaphase. The cells are then fixed and spotted onto microscope slides, treated with formaldehyde, washed, and dehydrated in ethanol. Probes are then added and the samples are analyzed by any of the techniques discussed below.

Cytology involves the examination of individual cells, nuclei and/or chromosome spreads from a biological sample. Cytological examination of a sample begins with obtaining a specimen of cells, which can typically be done by scraping, swabbing or brushing an area, as in the case of cervical specimens, or by collecting body fluids, such as those obtained from the chest cavity, bladder, or spinal column, or by fine needle aspiration or fine needle biopsy, as in the case of internal tumors. In a conventional manual cytological preparation, the sample is transferred to a liquid suspending material and the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. The cells/nuclei are then fixed on the microscope slide before analysis by any of the techniques discussed below.

In a traditional hybridization experiment using a cytological sample, slides containing the specimen are immersed in a methanol:acetic acid or formaldehyde buffer, washed, and then dehydrated in ethanol. The probes are then added and the specimen is covered with a coverslip. The slide is incubated at a temperature sufficient to denature any nucleic acid in the specimen (e.g., 5 minutes at 82° C.) and then incubated at a temperature sufficient to allow hybridization (e.g., overnight at 37° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

Histology involves the examination of cells/nuclei in thin slices of tissue. To prepare a tissue sample for histological examination, pieces of the tissue are fixed in a suitable fixative, typically an aldehyde such as formaldehyde or glutaraldehyde, and then embedded in melted paraffin wax. The wax block containing the tissue sample is then cut on a microtome to yield thin slices of paraffin containing the tissue, typically from 2 to 10 microns thick. The specimen slice is then applied to a microscope slide, air dried, and heated to cause the specimen to adhere to the glass slide. Residual paraffin is then dissolved with a suitable solvent, typically xylene, toluene, or others. These so-called deparaffinizing solvents are then removed with a washing-dehydrating type reagent prior to analysis of the sample by any of the techniques discussed below. Alternatively, slices may be prepared from frozen specimens, fixed briefly in 10% formalin or other suitable fixative, and then infused with dehydrating reagent prior to analysis of the sample.

In a traditional hybridization experiment using a histological sample, formalin-fixed paraffin embedded tissue specimens are cut into sections of 2-6 µm and collected on slides. The paraffin is melted (e.g., 30-60 minutes at 60° C.) and then removed (deparaffinated) by washing with xylene (or a xylene substitute), e.g., 2×5 minutes. The samples are rehydrated, washed, and then pre-treated (e.g., 10 minutes at 95-100° C.). The slides are washed and then treated with pepsin or another suitable permeabilizer, e.g., 3-15 minutes at 37° C. The slides are washed (e.g., 2×3 minutes), dehydrated, and probe is applied. The specimens are covered with a coverslip and the slide is incubated at a temperature sufficient to denature any nucleic acid in the specimen (e.g. 5 minutes at 82° C.), followed by incubation at a temperature sufficient to allow hybridization (e.g., overnight at 37° C.). After hybridization, the coverslips are removed and the specimens are subjected to a high-stringency wash (e.g., 10 minutes at 65° C.) followed by a series of low-stringency washes (e.g., 2×3 minutes at room temperature). The samples are then dehydrated and mounted for analysis.

1. Hybridization Techniques

The compositions and methods of the present disclosure can be used fully or partly in all types of RNA hybridization techniques known in the art for cytological and histological samples. Such techniques include, for example, in situ hybridization (ISH), fluorescent in situ hybridization (FISH; including multi-color FISH and Fiber-FISH), chromogenic in situ hybridization (CISH), silver in situ hybridization (SISH), and arrays. The compositions of the disclosure may improve the efficiency of traditional RNA hybridization applications by reducing the denaturation and hybridization temperatures and/or the time.

In general, molecular probes may be prepared by chemical synthesis, PCR, or by amplifying a specific DNA sequence by cloning, inserting the DNA into a vector, and amplifying the vector insert in appropriate $E$ $coli$ host cells. Commonly used vectors include bacterial plasmids, cosmids, bacterial artificial chromosomes (BACs), PI diverted artificial chromosomes (PACs), or yeast artificial chromosomes (YACs). The amplified DNA is then extracted and purified for use as a probe.

The nucleic acid probe may be a double or single stranded nucleic acid fragment or sequence, such as DNA, RNA, or analogs such as PNA or LNA. The probes may be labeled to make identification of the probe-target hybrid possible by use, for example, of a fluorescence or bright field microscope/scanner. In some embodiments, the probe may be labeled using radioactive labels such as $^{31}P$, $^{33}P$, or $^{32}S$, non-radioactive labels such as digoxigenin and biotin, or fluorescent labels.

In general, the type of probe determines the type of feature one may detect in a hybridization assay. For example, large insert probes may be used to target unique single-copy sequences. With these large probes, the hybridization efficiency is inversely proportional to the probe size. Smaller probes can be used to detect aberrations such as deletions, amplifications, inversions, duplications, and aneuploidy. For example, differently-colored locus-specific probes can be used to detect translocations via split-signal in situ hybridization.

In general, the ability to discriminate between closely related sequences is inversely proportional to the length of the hybridization probe because the difference in thermal stability decreases between wild type and mutant complexes as probe length increases. Probes of greater than 10 bp in length are generally required to obtain the sequence diversity necessary to correctly identify a unique organism or clinical condition of interest. On the other hand, sequence differences as subtle as a single base (point mutation) in very short oligomers (<10 base pairs) can be sufficient to enable the discrimination of the hybridization to complementary nucleic acid target sequences as compared with non-target sequences.

In certain embodiments, at least one set of the hybridization probes may comprise one or more PNA probes. Alternatively, or in addition, at least one set of the hybridization probes in any of the techniques discussed above may comprise one or more locked nucleic acid (LNA) probes. Due to the additional bridging bond between the 2' and 4' carbons, the LNA backbone is pre-organized for hybridization. LNA/RNA interactions are stronger than the corresponding DNA/RNA interactions, as indicated by a higher melting temperature. Thus, the compositions and methods of the disclosure, which decrease the energy required for hybridization, are particularly useful for hybridizations with LNA probes.

In one embodiment, the probes may comprise a detectable label (a molecule that provides an analytically identifiable signal that allows the detection of the probe-target hybrid). The detectable label may be directly attached to a probe, or indirectly attached to a probe by using a linker. Any labeling method known to those in the art, including enzymatic and chemical processes, can be used for labeling probes used in the methods and compositions of the disclosure. In other embodiments, the probes are not labeled.

In general, in situ hybridization techniques such as FISH, CISH, and SISH for DNA detection, employ large, mainly unspecified, nucleic acid probes that hybridize with varying stringency. Using large probes renders the in situ hybridization technique very sensitive. However, the successful use of large probes in traditional hybridization assays depends on blocking the undesired background staining derived from repetitive sequences that are present throughout the genome. Traditional methods for decreasing nonspecific probe binding include the use of unlabeled "blocking" DNA, such as Cot-1 DNA. In addition, nonspecific probe binding may be decreased by saturating the binding sites on proteins and tissue by incubating tissue with prehybridization solutions containing ficoll, bovine serum albumin (BSA), polyvinyl pyrrolidone, and nucleic acids.

Bound probes may be detected in cytological and histological samples either directly or indirectly with fluorochromes (e.g., FISH), organic chromogens (e.g., CISH), silver particles (e.g., SISH), or other metallic particles (e.g., gold-facilitated fluorescence in situ hybridization, GOLD-FISH). Thus, depending on the method of detection, populations of cells/nuclei obtained from a sample to be tested may be visualized via fluorescence microscopy or conventional brightfield light microscopy.

Hybridization assays on cytological and histological samples are useful tools for determining the number, size, and/or location of specific DNA or RNA sequences.

FISH may be used when multiple color imaging is required and/or when the protocol calls for quantification of signals. The technique generally entails preparing a cytological sample, labeling probes, optionally denaturing the target and the probe, hybridizing the probe to the target sequence, and detecting the signal. Typically, the hybridization reaction fluorescently stains the targeted sequences so that their location, size, or number can be determined using fluorescence microscopy, flow cytometry, or other suitable instrumentation. RNA sequences ranging from megabases down to several kilobases can be studied using FISH. With enhanced fluorescence microscope techniques, such as, for example, deconvolution, even a single mRNA molecule can be detected. FISH may also be used on metaphase spreads and interphase nuclei.

A useful application for FISH has been in detecting single-copy sequences, in particular disease related sequences in humans and other eukaryotic model species, and the detection of infectious agents. FISH may be used to detect chromosomal aneuploidy in prenatal diagnoses, hematological cancers, and solid tumors; gene abnormalities such as oncogene amplifications, gene deletions, or gene fusions; translocations, duplications, insertions, or inversions; contiguous gene syndromes such as microdeletion syndrome; the genetic effects of various therapies; and viral nucleic acids in somatic cells and viral integration sites in chromosomes. FISH techniques include multiplex FISH (m-FISH), spectral karyotyping (SKY), combined binary ration labeling (COBRA), color-changing karyotyping, cross-species color banding, high resolution multicolor banding, telomeric multiplex FISH (TM-FISH), split-signal FISH (ssFISH), and fusion-signal FISH.

CISH and SISH may be used for many of the same applications as FISH, and have the additional advantage of allowing for analysis of the underlying tissue morphology, for example in histopathology applications. If FISH is performed, the hybridization mixture may contain sets of distinct and balanced pairs of probes. For CISH, the hybridization mixture may contain at least one set of probes configured for detection with one or more conventional organic chromogens, and for SISH, the hybridization mixture may contain at least one set of probes configured for detection with silver particles, as described in Powell R D et al., "Metallographic in situ hybridization," Hum. Pathol., 38:1145-59 (2007).

The compositions of the disclosure may also be used fully or partly in all types of molecular biology techniques involving hybridization, including blotting and probing (e.g., northern blotting and southern blotting), and arrays.

2. Hybridization Conditions

Hybridization methods using the compositions of the disclosure may involve applying the compositions to a sample comprising a target nucleic acid sequence, most likely in a double stranded form. Usually, in order to secure access for the probe to hybridize with the target sequence, the sample and composition are heated to denature the target nucleic acids. During denaturation the solvent interacts with the sequence and facilitates the denaturation of the target and the re-annealing of the probe to target.

Hybridizations using the compositions of the disclosure may be performed using the same assay methodology as for hybridizations performed with traditional compositions. However, the compositions of the disclosure allow for shorter hybridization times. For example, the heat pretreatment, digestion, denaturation, hybridization, washing, and. mounting steps may use the same conditions in terms of volumes, temperatures, reagents and incubation times as for traditional compositions. A great variation exists in the traditional hybridization protocols known in the art. For example, some protocols specify a separate denaturation step of potential double stranded nucleotides without probe present, before the following hybridization step. The compositions of the disclosure may be used in any of traditional hybridization protocols known in the art.

Alternatively, assays using the compositions of the disclosure can be changed and optimized from traditional methodologies, for example, by decreasing the hybridization time, increasing or decreasing the denaturation and/or hybridization temperatures, and/or increasing or decreasing the hybridization volumes.

In certain embodiments, the compositions of the disclosure will produce strong signals when the denaturation temperature is from 60° C. to 100° C. and the hybridization temperature is from 20° C. to 60° C. In other embodiments, the compositions of the disclosure will produce strong signals when the denaturation temperature is from 60° C. to 70° C., 70° C. to 80° C., 70° C. to 90° C., 80° C. to 90° C., or 90° C. to 100° C., and the hybridization temperature is from 20° C. to 30° C., 30° C. to 40° C., 35° C. to 50° C., 40° C. to 50° C., or 50° C. to 60° C. In other embodiments, the compositions of the disclosure will produce strong signals when the denaturation temperature is 72° C., 73° C., 82° C., 85° C., or 92° C., and the hybridization temperature is 37° C., 40° C., 45° C., or 50° C.

In other embodiments, the compositions of the disclosure will produce strong signals when the denaturation time is from 0 to 10 minutes and the hybridization time is from 0 minutes to 24 hours. In other embodiments, the compositions of the disclosure will produce strong signals when the denaturation time is from 0 to 5 minutes and the hybridization time is from 0 minutes to 8 hours. In other embodiments, the compositions of the disclosure will produce strong signals when the denaturation time is 0, 1, 2, 3, 4, or 5 minutes, and the hybridization time is 0 minutes, 5 minutes, 15 minutes, 30 minutes, 60 minutes, 120 minutes, 180 minutes, or 240 minutes. It will be understood by those skilled in the art that in some cases for RNA detection, a denaturation step is not required.

Accordingly, hybridizations using the compositions of the disclosure may be performed in less than 8 hours. In other embodiments, the hybridization is performed in less than 6 hours. In still other embodiments, the hybridization is performed within 4 hours. In other embodiments, the hybridization is performed within 3 hours. In yet other embodiments, the hybridization is performed within 2 hours. In other embodiments, the hybridization is performed within 1 hour. In still other embodiments, the hybridization is performed within 30 minutes. In other embodiments, they hybridization can take place within 15 minutes. The hybridization can even take place within 10 minutes or in less than 5 minutes.

As hybridization time changes, the concentration of probe may also be varied in order to produce strong signals and/or reduce background. For example, as hybridization time decreases, the amount of probe may be increased in order to improve signal intensity. On the other hand, as hybridization time decreases, the amount of probe may be decreased in order to improve background staining.

The compositions of the disclosure often allow for better signal-to-noise ratios than traditional hybridization compositions. For example, with certain probes, a one hour hybridization with the compositions of the disclosure will produce similar background and stronger signals than an overnight hybridization in traditional compositions. Background is not seen when no probe is added.

Traditional assay methods may also be changed and optimized when using the compositions of the disclosure depending on whether the system is manual, semi-automated, or automated. For example, a semi- or an automated system will benefit from the short hybridization times obtained with the compositions of the disclosure. The short hybridization time may reduce the difficulties encountered when traditional compositions are used in such systems. For example, one problem with semi- and automated systems is that significant evaporation of the sample can occur during hybridization, since such systems require small sample volumes (e.g., 10-150 µL), elevated temperatures, and extended hybridization times (e.g., 14 hours). Thus, proportions of the components in traditional hybridization compositions are fairly invariable. However, since the compositions of the disclosure allow for faster hybridizations, evaporation is reduced, allowing for increased flexibility in the proportions of the components in hybridization compositions used in semi- and automated systems.

Another problem with automated imaging analysis is the number of images needed, the huge amount of storage place required, and the time required to take the images. The compositions of the disclosure can produce very strong signals compared to traditional compositions. Because of the very strong signals produced by the compositions of the disclosure, the imaging can be done at lower magnification than required for traditional compositions and can still be detected and analyzed by algorithms. Since the focal plane becomes wider with lower magnification, the compositions of the disclosure can reduce or eliminate the requirement to take serial sections of a sample. As a result, the overall imaging may be much faster, since the compositions of the disclosure require fewer or no serial sections and each image covers much greater area. In addition, the overall time for analysis can be faster, since the total image files are much smaller.

The present invention has multiple aspects, illustrated by the following non-limiting examples.

3. Examples

Example 1

Hybridization Buffer Composition for FISH Assay

Dextran sulfate, saline sodium citrate, formamide, and guanidinium thiocyanate were combined to make hybridization buffer compositions 1-4. The formulations in the table are the final working concentrations in 15 µL reaction, which uses 12 µL of the bulk buffer and 3 µL of aqueous probe mixture. Dextran sulfate, saline sodium citrate, formamide, guanidinium thiocyanate and sodium poly acrylate (avg. MW of 2,100 g/mol or 5,100 g/rnol) were combined to make hybridization buffer composition 5. Dextran sulfate, saline sodium citrate, formamide, and ethylene carbonate were combined to make hybridization buffer composition 6. Dextran sulfate, saline sodium citrate, formamide, and dimethyl succinate were combined to make hybridization buffer composition 7. The components of the buffer compositions and their concentrations are detailed in Table 1.

Buffer preparations: 1 mL size/volume buffers were prepared. For each buffer tube, dextran sulfate was added in small portions to a solution of guanidinum thiocyanate, Milli-Q water (~⅓-⅔ of total water in buffer), formamide and 20× SCC buffer. Buffers were agitated for at least 12 hours prior to final pH validation and volume adjustment.

TABLE 1

| Buffer Comp. | Dextran sulfate (w/v) | Saline sodium citrate (X) | Formamide (v/v) | Guanidinium thiocyanate (M) | Sodium polyacrylate (w/v) | Dimethyl succinate (w/v) | Ethylene carbonate (w/v) |
|---|---|---|---|---|---|---|---|
| 1 | 28.8% | 0.4X | 40% | 1.6M | — | — | — |
| 2 | 32% | 0.4X | 40% | 1.6M | — | — | — |
| 3 | 24% | 0.5X | 33% | 1.0M | — | — | — |

TABLE 1-continued

| Buffer Comp. | Dextran sulfate (w/v) | Saline sodium citrate (X) | Formamide (v/v) | Guanidinium thiocyanate (M) | Sodium polyacrylate (w/v) | Dimethyl succinate (w/v) | Ethylene carbonate (w/v) |
|---|---|---|---|---|---|---|---|
| 4 | 28% | 0.5X | 30% | 1.0M | — | — | — |
| 5 | 18% | 1.0X | 33% | 1.0M | 10% | — | — |
| 6 | 22.3% | 2.3X | 22.3% | — | — | — | 12% |
| 7 | 22.3% | 2.3X | 22.3% | — | — | 17.6% | — |

Example 2

Evaluation of FISH Assay with Hybridization Buffer Compositions

The FISH performance of hybridization buffers 3, 4 and 5 were evaluated using a three color BCR (Spectrum Orange)/ABL (Spectrum Green)/ASS (Spectrum Aqua) probe set. ThermoBrite co-denaturation was performed at 80° C. for 2 minutes, followed by hybridizations at 37° C. for 2 hours.

The hybridization performance of each buffer was assessed based on quality ratings of intensity, specificity, background and cross-hybridization by at least 2 independent reviewers (1-5 scale, where 5 is the best), using the following microscope filters: single band-pass aqua, green and orange and triple band-pass (orange/green/DAPI). Table 2 reports the results of the performance of the buffer compositions in the FISH assay, listing mean intensity, average specificity, average background and overall rating (determined by the lowest value of intensity, specificity and background for probe signal in the hybridization) for all filters, as well as mean overall ratings by filter. Buffer 4 scored well, as its mean overall rating (determined by the lowest value of intensity, specificity and background for probe signal in the hybridization) was 3.9 and its mean overall rating with the triple pass filter was 4.0.

Dextran Sulfate: 0.35 g DS/mL Buffer×1mL B/1.20 g B*100=29.1 wt. %
Formamide: 0.375 mL F/mL B×1.13 gF/mL F×1 mL B/1.20 g B×100=34.2 wt. %
Guanidine thiocyanate (GITC): 0.148 g G/mL B×1 mL B/1.20 g B=12.3 wt. %
NaCl: 0.0312 mL SSC/mLB×3 mmol NaCl/mL SSC× 0.0585 g NaCl/mmol NaCl×1 mL B/1.2 g B×100=0.45%
Sodium Citrate: 0.0312 mL SSC/mLB×0.3 mmol SC/mL SSC×0.294 g SC/mmol SC×1 mL B/1.2 g B×100=0.23%
Water (by difference)=23.7%
Water (based on minibulk actual recipe)=30 mL W/100 mL B×1 mL B/1.2 g B=25.0% (note 20 mL water added initially and addn. 10 mL added for QS)

Hybridization buffer composition 4 can be prepared with the components as shown in Table 3. To make a working solution, 12 μL of this buffer was used with 3 μL of aqueous probe mixture in the hybridization reaction.

TABLE 3

| Buffer Comp. | Dextran sulfate | Saline sodium citrate | Formamide | Guanidinium thiocyanate | Initial Water | Total |
|---|---|---|---|---|---|---|
| 4 | 0.350 g | 0.031X | 0.375 mL | 0.148 g | 0.200 mL | 1.0 mL |

TABLE 2

| Buffer | Mean Intensity | Mean Specificity | Mean Background | Mean OA | Mean Aqua Overall | Mean Green Overall | Mean Orange Overall | Mean Tr Overall |
|---|---|---|---|---|---|---|---|---|
| 1 | 4.0 | 4.0 | 3.9 | 3.9 | 3.5 | 3.9 | 3.8 | 4.0 |
| 2 | 4.3 | 3.9 | 4.0 | 3.9 | 4.0 | 3.8 | 4.0 | 3.8 |
| 3 | 3.9 | 3.9 | 4.0 | 3.7 | 3.4 | 3.7 | 3.6 | 4.0 |
| 4 | 4.1 | 4.1 | 4.1 | 3.9 | 3.6 | 3.9 | 4.0 | 4.0 |
| 5 | 3.9 | 4.1 | 4.1 | 3.8 | 3.2 | 3.9 | 4.1 | 4.0 |
| 6 | 3.3 | 3.8 | 3.6 | 3.3 | 3.0 | 3.5 | 3.5 | 3.3 |
| 7 | 3.0 | 3.4 | 3.4 | 3.0 | 3.0 | 2.9 | 3.1 | 3.0 |

The bulk buffer composition comprises, by weight, approximately 23.7% water, 34.2% formamide, 29.1% dextran sulfate, 12.3% guanidine thiocyanate, 0.45% sodium chloride and 0.23% sodium citrate based on density.

The buffer density is 1.20 g/mL.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A hybridization buffer composition comprising, by weight, about 29.1% dextran sulfate, about 0.23% sodium citrate, about 0.45% sodium chloride, about 34.2% formamide, about 12.3% guanidinium thiocyanate, and about 23.7% water.

2. The hybridization buffer composition of claim 1, further comprising a polyacrylate.

3. The hybridization buffer composition of claim 2, wherein the polyacrylate is about 5% to about 20%.

4. The hybridization buffer composition of claim 2, wherein the polyacrylate is sodium polyacrylate.

5. A hybridization composition comprising at least one nucleic acid sequence and the hybridization buffer composition of claim 1.

6. A hybridization composition comprising a first nucleic acid sequence, a second nucleic acid sequence and the hybridization buffer composition of claim 1, wherein the first nucleic acid sequence is a molecular probe.

7. A hybridization composition comprising at least 3 nucleic acid sequences and the hybridization buffer composition of claim 1, wherein at least 2 of the at least 3 nucleic acid sequences are molecular probes.

8. A method of combining nucleic acid sequences comprising: combining a first nucleic acid sequence, a second nucleic acid sequence, and the hybridization buffer composition of claim 1.

9. The method of claim 8, further comprising denaturing the first nucleic acid sequence and the second nucleic acid sequence.

10. The method of claim 8, further comprising hybridizing the first nucleic acid sequence and the second nucleic acid sequence.

11. A method of combining nucleic acid sequences comprising:
   combining an in situ biological sample comprising at least one nucleic acid sequence with the hybridization composition of claim 5.

12. The method of claim 11, further comprising denaturing the at least one nucleic acid sequence at a temperature range from about 70° C. to about 90° C.

13. The method of claim 11, further comprising hybridizing the at least one nucleic acid sequence to the in situ biological sample.

14. The method of claim 13, wherein said hybridizing the at least one nucleic acid sequence to the in situ biological sample takes place at a temperature range from about 35° C. to about 50° C.

15. The method of claim 12, wherein said hybridizing the at least one nucleic acid sequence to the in situ biological sample is complete in 5 hours or less 4 hours or less, 3 hours or less, 2 hours or less, 1 hour or less, 30 minutes or less, 15 minutes or less, or 5 minutes or less.

16. The method of claim 8, wherein the first nucleic acid sequence is double stranded and the second nucleic acid is single stranded.

17. The method of claim 11, wherein the biological sample is a cytological or histological sample.

\* \* \* \* \*

UNITED STATES PATENT AND TRADEMARK OFFICE
CERTIFICATE OF CORRECTION

PATENT NO. : 10,457,981 B2
APPLICATION NO. : 15/256146
DATED : October 29, 2019
INVENTOR(S) : Klara Abravaya et al.

Page 1 of 1

It is certified that error appears in the above-identified patent and that said Letters Patent is hereby corrected as shown below:

In the Claims

Claim 15, Column 18, Line 20, after "sample is complete in 5 hours or less" insert -- , --.

Signed and Sealed this
Eighteenth Day of February, 2020

Andrei Iancu
*Director of the United States Patent and Trademark Office*